United States Patent [19]

Haus et al.

[11] Patent Number: 5,110,971
[45] Date of Patent: May 5, 1992

[54] SILYL DERIVATIVES OF EUGENOL

[75] Inventors: Mary K. Haus, Monroeville Boro, Allegheny County; Andrew J. Sivak, Edgewood Boro, Allegheny County, both of Pa.

[73] Assignee: Aristech Chemical Corporation, Pittsburgh, Pa.

[21] Appl. No.: 577,713

[22] Filed: Sep. 5, 1990

Related U.S. Application Data

[63] Continuation-in-part of Ser. No. 438,560, Nov. 20, 1989, abandoned, which is a continuation of Ser. No. 375,648, Jul. 5, 1989, abandoned.

[51] Int. Cl.$^5$ .............................. C07F 7/08; C07F 7/18
[52] U.S. Cl. .................................................. 556/446
[58] Field of Search ........................................ 556/446

[56] References Cited

U.S. PATENT DOCUMENTS

| 2,707,191 | 4/1955 | Martin et al. | 556/446 X |
| 3,137,720 | 2/1964 | Cooper | 556/446 X |
| 3,491,137 | 1/1970 | Zaweski et al. | 556/446 X |
| 4,332,957 | 6/1982 | Braus et al. | 556/446 |
| 4,372,835 | 2/1983 | Chung et al. | 204/159.13 |
| 4,783,495 | 11/1988 | Pastor et al. | 556/446 X |
| 4,916,248 | 4/1990 | Brownell et al. | 556/486 |

FOREIGN PATENT DOCUMENTS 0746498  3/1956  United Kingdom ................. 556/446

OTHER PUBLICATIONS

PCT International Publication No. WO 88/08856 (also identified as International Application No. PCT/US87/03454), Sivak et al., "Incorporation of Functional Groups in Polymers", Nov. 17, 1988, pp. 1–56.

Horiguchi et al., "High Molecular Weight Polysilanes with Phenol Moieties", Macromolecules, vol. 21, No. 2, pp. 304–309, 1988.

*Primary Examiner*—Paul F. Shaver
*Attorney, Agent, or Firm*—William L. Krayer

[57] ABSTRACT

Silyl derivatives of eugenol include compositions of the formula

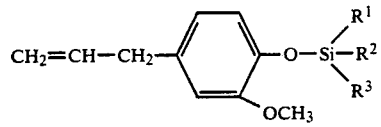

where $R^1$, $R^2$ and $R^3$ are independently selected from linear, branched, and cyclic hydrocarbon groups having a total of from one to about eight carbon atoms, except that where one of $R^1$, $R^2$ or $R^3$ is a phenyl group, the total of carbon atoms must be at least nine. They may be made by silylating the corresponding hydroxyl compound. They are useful as comonomers for olefins to introduce functional sites and may be copolymerized in Ziegler-Natta catalyst systems.

5 Claims, No Drawings

SILYL DERIVATIVES OF EUGENOL

RELATED APPLICATION

This is a continuation-in-part of U.S. patent application Ser. No. 438,560 filed Nov. 20, 1989, which is a continuation of U.S. patent application Ser. No. 375,648 filed Jul. 5, 1989, now abandoned, both bearing the title SILYL DERIVATIVES OF EUGENOL.

TECHNICAL FIELD

This invention relates to new silyl derivatives of a certain substituted phenol, specifically to silyl derivatives of eugenol, known also as 2-methoxy-4-(2-propenyl) phenol or 4-allyl-2-methoxyphenol, which may be used to copolymerize with lower olefins, particularly propylene. In particular, it relates to compositions of the formula

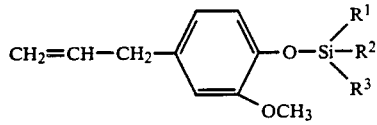

wherein $R^1$, $R^2$ and $R^3$ are independently selected from linear, branched, and cyclic hydrocarbon groups having a total of from eight to twenty-four carbon atoms, except that, where one of $R^1$, $R^2$ and $R^3$ is a phenyl group, the total carbon atoms must be at least nine.

BACKGROUND ART

In U.S. patent application Ser. No. 047,960 (see corresponding PCT International Publication No. WO88/08856, Nov. 17, 1988), it is disclosed that comonomers for propylene may be made by protecting the oxygen of a copolymerizable hydroxy-containing compound by substituting the hydrogen thereof with a silyl group having a minimum steric bulk, i.e., at least about three carbon atoms surrounding it, so that they may be copolymerized in a Ziegler-Natta system. Silylated monomers of the general formula

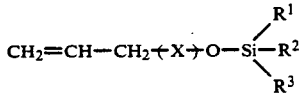

where X can be a variety of connecting moeities, are suggested in the publication.

The peculiar advantage, however, of eugenol as a potential comonomer in its silylated form apparently has not been seen in the prior art, in spite of the fact that a different silylated monomer has been formed from trimethylsilylated eugenol. See Horiguchi et al "High Molecular Weight Polysilanes with Phenol Moeities" Macromolecules, 1988, pp. 304–309.

DISCLOSURE OF INVENTION

The invention herein is a series of new compounds of the formula

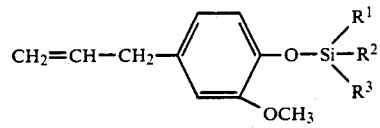

where $R^1$, $R^2$ and $R^3$ are independently selected from linear, branched, and cyclic hydrocarbon groups having a total from eight to twenty-four carbon atoms, except that, where one of $R^1$, $R^2$ and $R^3$ is a phenyl group, the total carbon atoms must be at least nine.

In order to define the invention, several eugenol derivatives have been prepared as described in the following examples.

All manipulations were performed under inert atmosphere using standard Schlenk techniques. All liquid reagents and solvents were purged with argon prior to their introduction into the reaction system.

COMPARATIVE EXAMPLE 1

(4-allyl-2-methoxy) phenoxy trimethyl silane 50 g (0.304 mol) of eugenol were added to a 500 ml round bottom flask followed by 100 ml of toluene. The flask was cooled to 0° C. with stirring and 7.000 g (0.304 mol) sodium chunks were added in two aliquots. The sodium phenoxide began to precipitate immediately and after approximately 1 hour, 200 ml of toluene and 300 ml of tetrahydrofuran were added to the cooled solution. The cold bath was removed one-half hour after this addition of solvent. Upon warming to room temperature, the sodium salt of eugenol dissolved and produced a clear solution. The mixture was stirred at room temperature for four hours at which time an ice bath was applied. 36.286 g (0.334 mol) of Me₃SiCl were added dropwise over a period of 1.5 hours. The solution was allowed to warm to room temperature and was stirred overnight.

475 ml of heptane were then added to the mixture and the precipitate was allowed to settle out for one hour. The resultant colloidal mixture was filtered through fritted glass/Celite and produced a murky green solution. Low boiling impurities (under 120° C.) were removed by an atmospheric distillation. The product was isolated by vacuum distillation and was collected at 93-95° C. (1 mm Hg). Approximately 60 g of the product was collected (83% yield).

EXAMPLE 2

(4-allyl-2-methoxy) phenoxy dimethylphenyl silane 34.11 g (0.208 mol) of eugenol were added to a 500 ml Schlenk flask followed by 0.3 g of sodium. 35.16 g (0.195 mol) of dimethylphenyl (ethoxy) silane were then added dropwise to this stirred solution. 80 ml of tetrahydrofuran were then added to dissolve the precipitated sodium phenoxide and the mixture was stirred overnight.

Atmospheric distillation removed the tetrahydrofuran and approximately 10 ml of ethanol. Vacuum distillation (~0.5 mm Hg) yielded 48 g (82% yield) of the desired product which was collected at 163°-165° C. Identification of this product was accomplished by ¹H NMR and gcms.

EXAMPLE 3

The procedure in Example 2 was employed to prepare (4-allyl-2-methoxy) phenoxy diphenylmethyl silane.

EXAMPLE 4

Preparation of (4-allyl-2-methoxy) phenoxy (tert-butyl)diphenyl silane

To a 500 ml round bottom flask with argon inlet were added 29.88 g (0.182 mol) of eugenol. To this stirred solution were then added 14.40 g (0.182 mol) of pyridine followed by 80 ml of heptane. An addition funnel was then added to the setup and to this were added 50 g (0.182 mol) of tert-butyl(diphenyl)chlorosilane. The silane reagent was added dropwise over a period of 1 hour and during this time a small amount of pyridinium hydrochloride precipitated out of the solution. Since the rate of reaction was slow the addition funnel was replaced by a condenser and the mixture was refluxed for 2 days at which time 150 ml of heptane were added and the solution was filtered and transferred to a clean 500 ml flask equipped with a sidearm. The product distilled at 175°-185° C. (0.5 mm Hg) and the purity was determined to be 82% by gcms.

EXAMPLE 5

Preparation of (4-allyl-2-methoxy) phenoxy(thexyl)dimethylsilane

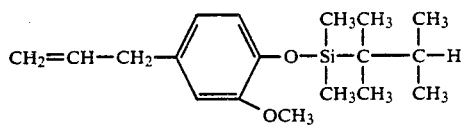

To a 500 ml round bottom flask with argon inlet were added 45.29 g (0.280 mol) of eugenol. To this stirred solution were then added 22.15 g (0.280 mol) of pyridine followed by 60 ml of heptane. An addition funnel was then added to the setup and to this were added 50 g (0.280 mol) of thexyl(dimethyl)chlorosilane. The silane reagent was added dropwise over a period of 1 hour and during this time a very small amount of pyridinium hydrochloride precipitated out of the solution. The mixture was stirred at room temperature for two days at which time 150 ml of heptane were added and the solution was filtered and transferred to a clean 500 ml flask equipped with a sidearm. The product distilled at 140°-145° C. (0.5 mm Hg) and the purity was determined to be 98% by gcms and $^1$H nmr.

EXAMPLE 6

Preparation of (4-allyl-2-methoxy) phenoxy (tri-n-propyl) silane

To a 1000 ml round bottom flask with argon inlet were added 49.26 g (0.300 mol) of eugenol. To this stirred solution were then added 23.73 g (0.300 mol) of pyridine followed by 60 ml of heptane. An addition funnel was then added to the setup and to this were added 57.84 g (0.300 mol) of (tri-n-propyl)chlorosilane. The silane reagent was added dropwise over a period of 1 hour and during this time pyridinium hydrochloride began to precipitate out of the solution. The mixture was stirred at room temperature for 18 hours at which time 300 ml of heptane were added and the solution was filtered and transferred to a clean 500 ml flask equipped with a sidearm. The product distilled at 120°-123° C. (0.5 mm Hg).

Following are polymerization examples:

Standard inert atmosphere techniques were used to exclude moisture and oxygen throughout the manipulations recited below to copolymerize the freshly prepared monomer such as the products of examples 1-3 with lower olefins.

A round bottom flask fitted with a side arm, magnetic stirring bar and a stopper, which apparatus had been assembled hot from a drying oven and was then either evacuated and refilled with inert gas several times or (and) purged with the inert gas for at least 15 minutes, was charged with a given amount of solvent, heptane or toluene, usually 125 ml. The solvents were freshly distilled from sodium and triethyl aluminum (TEA) over which they had been refluxing for at least 18 hours under an inert atmosphere. Immediately after the solvent had been charged to the flask a given amount (generally 1 to 50 ml) of alkyl aluminum co-catalyst, which was in the form of a heptane solution of about 25 wt. % (0.715 g/ml in heptane), was also added to the flask which was then lowered into a thermostated oil bath and magnetic stirring was begun.

At this point the inert gas atmosphere in the flask was replaced with the gaseous comonomer by a minimum of 3 cycles of evacuation and refilling back to atmospheric pressure with the comonomer. After the third cycle, the solution was stirred for at least 10 minutes (usually longer) to allow the solvent to become saturated with the comonomer. Pressure was maintained at about one atmosphere via a bubbler.

Next were added an "external donor", which usually was diphenyl dimethoxy silane or phenyl triethoxy silane, if one was being used, and the other comonomer. The polymerization was initiated by the addition of the transition metal containing co-catalyst, which was a titanium tetrachloride on a magnesium chloride support.

As the gaseous comonomer was consumed it was replaced by maintaining the pressure constant at one atmosphere via a bubbler.

After a specified period of time (generally about 1 to 3 hours) the reaction was quenched by the addition of acidified alcohol (HCl in iso-propanol, ethanol, and/or methanol). The quenched reaction slurry was combined with the alcohol solution of volume at least twice the original volume of the inert reaction solvent. The resultant slurry was stirred for at least 45 minutes and then filtered. This hydrolysis treatment (alcoholysis) not only stopped the reaction, it dissolved catalyst residues and removed the silyl groups and thus regenerated the hydroxyl groups.

If the filtration proceeded very slowly, the slurry was combined with enough water to make the filtration proceed at a convenient rate.

The polymer was resuspended in alcohol, stirred, filtered and vacuum dried overnight. Boiling heptane soluble content was determined by standard methods.

COMPARATIVE EXAMPLE 7

Copolymerization of propylene and (2-methoxy-4-allyl) phenoxy dimethylphenyl silane A 500 ml round bottom flask equipped with an argon inlet was evacuated and refilled with inert gas three times. To this flask were added 125 ml of dry, degassed heptane followed by 5.5 ml (0.018 mol) of 2-methoxy-4- allyl) phenoxy dimethylphenyl silane (see Example 2). The solution was subsequently saturated with propylene and 5.4 ml of the triethylaluminum co-catalyst (0.715 g/ml in heptane) was added. The Al/Si ratio was varied between 0.2 and 0.5 and an external modifier (an alkoxy silane) was used in some polymerizations.

The flask was then lowered into an oil bath which had been maintained at 50° C. and 0.153 g of titanium co-catalyst were added which initiated the polymerization. The reaction proceeded for two hours before being quenched by the addition of approximately 300 ml of acidified isopropanol. This solution was allowed to stir for one hour at which time the product was filtered, resuspended in isopropanol, and stirred for one-half hour. The polymer was then filtered and vacuum dried. Upon removal (hydrolysis) of the silyl groups and regeneration of the hydroxyl groups now on the copolymer chain, various functional groups such as dyes can be substituted on the hydroxyl groups.

COMPARATIVE EXAMPLES 8 and 9

Procedures similar to Example 7 were followed to copolymerize with propylene the (4-allyl-2-methoxy) phenoxy trimethyl silane of Example 1, the (4-allyl-2-methoxy) phenoxy diphenylmethyl silane of Example 3, and the comonomers of Examples 4, 5 and 6, with the results shown for different concentrations of silane monomers and aluminum catalyst component to silane as shown in Table I.

carbons in the silyl group was necessary for a reasonable yield of polymer to be obtained.

Although many practical applications may be proposed for the copolymers of propylene with 0.1 to 0.5 mole percent of our silylated eugenol derivatives, such as adhesives, dyed polypropylene, and compatibilizers, our monomers are also useful for copolymerizing in Ziegler-Natta systems with other lower olefins (as well as propylene alone) such as ethylene, butene and/or mixtures of them with propylene in amounts from about 0.01 mole percent to as much as 50 mole percent or more of the eugenol derivatives. A preferred range is about 0.05 mole percent to about 5 mole percent eugenol derivative.

We claim:

1. A compound of the formula

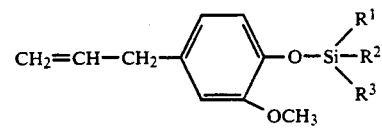

in which $R^1$, $R^2$ and $R^3$ are independently selected from linear, branched, and cyclic hydrocarbon groups having a total of from eight to twenty-four carbon atoms, except that, where one of $R^1$, $R^2$ or $R^3$ is a phenyl group, the total carbon atoms must be at least nine.

2. (4-allyl-2-methoxy) phenoxy methyl diphenyl silane.

TABLE I

Glassware Copolymerization of Eugenol Derivatives with Propylene

| Run | Comonomer | [comonomer] moles/l | Al/Si | mod.* | polymer yield (g/g cat) | mol % phenol |
|---|---|---|---|---|---|---|
| 603 | (4-allyl-2-methoxy) phenoxy trimethyl silane | 0.14 | 0.44 | No | 46.2 | ** |
| 604 | | 0.37 | 0.20 | No | 9.3 | ** |
| 609 | (4-allyl-2-methoxy) phenoxy dimethylphenylsilane | 0.15 | 0.43 | No | 43.8 | 0.93# |
| 610 | | 0.37 | 0.20 | No | 4.5 | 4.4# |
| 809 | | 0.16 | 0.43 | No | 47 | 0.52# |
| 810 | | 0.16 | 0.43 | Yes | 50 | 0.36# |
| 888 | (4-allyl-2-methoxy) phenoxy tri-n-propylsilane | 0.15 | 0.48 | Yes | 89.3 | ** |
| 889 | | 0.40 | 0.49 | Yes | 103 | ** |
| 614 | (4-allyl-2-methoxy) phenoxy diphenylmethylsilane | 0.14 | 0.45 | No | 53.8 | ** |
| 615 | | 0.38 | 0.20 | No | 17.7 | ** |
| 751 | (4-allyl-2-methoxy) phenoxy (tert-butyl)diphenyl silane | 0.16 | 0.48 | Yes | 125 | 0.05# |
| 795 | | 0.13 | 0.49 | No | 65 | ** |
| 794 | | 0.13 | 0.46 | Yes | 85 | ** |
| 797 | | 0.36 | 0.52 | Yes | 122 | >.05# |
| 796 | | 0.38 | 0.47 | No | 60 | 0.48# |
| 753 | | 0.48 | 0.51 | Yes | 114 | 0.30# |
| 759 | (4-allyl-2-methoxy) phenoxy (thexyl)dimethylsilane | 0.14 | 0.48 | Yes | 139 | 0.21 |
| 760 | | 0.14 | 0.45 | No | 78 | 0.11 |
| 761 | | 0.26 | 0.21 | Yes | 62 | ** |

[propene] = 0.353M for all runs listed.
*external modifier (eg. alkoxy silane).
**no data.
NMR indicates incomplete removal of the silyl group.

It may be observed from Table I that the polymer yield (g/g catalyst) was significantly improved when the silyl protecting group did not contain a pheny substituent and was composed of eight or more carbons. When a phenyl group was present as one of the substituents on the silicon, it appeared that a minimum of nine lane.

3. (4-allyl-2-methoxy) phenoxy tert-butyl diphenyl silane.

4. (4-allyl-2methoxy) phenoxy thexyl dimethyl silane.

5. (4-allyl-2-methoxy) phenoxy tri-n-propyl silane.

* * * * *

UNITED STATES PATENT AND TRADEMARK OFFICE
CERTIFICATE OF CORRECTION

PATENT NO. : 5,110,971

DATED : May 5, 1992

INVENTOR(S) : Mary K. Hays and Andrew J. Sivak

It is certified that error appears in the above-identified patent and that said Letters Patent is hereby corrected as shown below:

ON THE TITLE PAGE:

Item [19], change "Haus et al" to --Hays et al ;

[75], change "Mary K. Haus, Monroeville Boro," to --Mary K. Hays, Monroeville Boro, Allegheny County,--.

Column 2, line 12, change "R" to -- $R^1$ --.

Column 3, lines 8 and 9, change "(tert-butyl)diphenyl silane" to -- (tert-butyl)diphenyl silane --;

line 15, change "tert-butyl(diphenyl)chlorosilane" to -- tert-butyl(diphenyl)chlorosilane --;

line 56, change "(tri-n-propyl) silane" to -- (tri-n-propyl) silane --;

line 62, change "(tri-n-propyl)chlorosilane" to -- (tri-n-propyl)chlorosilane --.

Column 5, Table I, Run 751, under "Comonomer", change "phenoxy (tert-butyl)diphenyl silane" to -- phenoxy (tert-butyl)diphenyl silane --.

Column 5, line 63, change "pheny" to -- phenyl --.

UNITED STATES PATENT AND TRADEMARK OFFICE
CERTIFICATE OF CORRECTION

PATENT NO. : 5,110,971

DATED : May 5, 1992

INVENTOR(S) : Mary K. Hays and Andrew J. Sivak

It is certified that error appears in the above-identified patent and that said Letters Patent is hereby corrected as shown below:

Column 6, line 64, claim 4, change "(4-allyl-2methoxy)" to --(4-allyl-2-methoxy)--.

Signed and Sealed this

Tenth Day of August, 1993

Attest:

MICHAEL K. KIRK

*Attesting Officer*     Acting Commissioner of Patents and Trademarks